United States Patent
Schulze et al.

(10) Patent No.: US 8,778,157 B2
(45) Date of Patent: Jul. 15, 2014

(54) DETECTING ANALYTES

(75) Inventors: Holger Schulze, Edinburgh (GB); Till Bachmann, Edinburgh (GB); Andrew Mount, Edinburgh (GB)

(73) Assignee: ITI Scotland Limited, Glasgow (GB)

( * ) Notice: Subject to any disclaimer, the term of this patent is extended or adjusted under 35 U.S.C. 154(b) by 629 days.

(21) Appl. No.: 12/921,902

(22) PCT Filed: Mar. 11, 2009

(86) PCT No.: PCT/EP2009/052884
§ 371 (c)(1),
(2), (4) Date: Oct. 21, 2010

(87) PCT Pub. No.: WO2009/112537
PCT Pub. Date: Sep. 17, 2009

(65) Prior Publication Data
US 2011/0031123 A1    Feb. 10, 2011

(30) Foreign Application Priority Data
Mar. 11, 2008   (GB) .................... 0804491.9

(51) Int. Cl.
*G01N 27/447* (2006.01)
*G01N 27/327* (2006.01)

(52) U.S. Cl.
USPC ....................... 204/547; 205/777.5

(58) Field of Classification Search
USPC ............... 204/437, 643, 409, 403.01, 547; 205/777.5, 792, 778
See application file for complete search history.

(56) References Cited

U.S. PATENT DOCUMENTS

| | | | |
|---|---|---|---|
| 5,569,367 A | 10/1996 | Betts et al. | |
| 2005/0003396 A1 | 1/2005 | Ozkan et al. | |
| 2005/0112645 A1 * | 5/2005 | Segawa et al. | 435/6 |
| 2006/0115828 A1 * | 6/2006 | Palmieri et al. | 435/6 |

FOREIGN PATENT DOCUMENTS

| | | | | |
|---|---|---|---|---|
| EP | 1643250 A1 * | 4/2006 | | G01N 33/53 |
| JP | 2001-165905 | 6/2001 | | |
| JP | 2006-47153 | 2/2006 | | |
| WO | 9938612 A | 8/1999 | | |

OTHER PUBLICATIONS

Washizu et al. "Electrostatic Manipulation of DNA in MIcrofabricated Structures," IEEE Transactions on Industry Applications, vol. 26, No. 6, Nov./Dec. 1990.*
Urdaneta et al., "Multile frequency dielectrophoresis," Electrophoresis, 2007, pp. 3145-3155, vol. 28, No. 18.
Landre, Julien, International Search Report, PCT/EP09/052884, European Patent Office, Jun. 16, 2009.
Nagatani, Ushio, Japanese Patent Application No. 2010-550197, Japanese Patent Office, Feb. 26, 2013.

* cited by examiner

*Primary Examiner* — Alex Noguerola
(74) *Attorney, Agent, or Firm* — Joseph R. Baker, Jr.; Gavrilovich, Dodd & Lindsey LLP

(57) ABSTRACT

Provided is a method for processing a sample, which method comprises:
a) contacting a binding phase, which binding phase is capable of binding an analyte, with the sample in the presence of a medium;
b) applying across the medium a first alternating field composed of a plurality of pulses and having a first frequency, a first pulse duration and a first pulse rise time;
c) optionally applying across the medium a second alternating field; and
d) thereby influencing the sample and/or the binding phase in the medium.

23 Claims, 8 Drawing Sheets

DETECTING ANALYTES

CROSS REFERENCE TO RELATED APPLICATIONS

This application is a U.S. National Stage Application filed under 35 U.S.C. §371 and claims priority to International Application No. PCT/EP2009/052884, filed Mar. 11, 2009, which application claims priority to Great Britain Application No. 0804491.9, filed on Mar. 11, 2008, the disclosure of which are incorporated herein by reference.

The present invention relates to a method for detecting an analyte using dielectrophoresis to obtain data on the analyte. The method is advantageous since it may result in enhanced speed and sensitivity over known assay methods.

Heterogeneous capture probe based assays have been used in the field of biological analyte detection for a number of years. For example, target nucleic acids may be detected by hybridisation of the target nucleic acid to a probe nucleic acid. Recently, DNA chips and microarrays have been used to detect target nucleic acids, which present multiple probe nucleic acids immobilized on a substrate.

A number of different approaches have been used to try to improve the efficiency of binding the target analyte to the capture probe or solid surface. For example, the mixing conditions in the reaction space can be optimized or the capture probe or solid surface can be immobilized into the medium by using beads as the solid phase. However, the speed and efficiency of these methods is limited by the diffusional boundary layer which cannot be removed by mixing or convection. Accordingly, improved methods for binding target analytes to a capture probe or solid surface, particularly for DNA hybridisation, have focused on employing additional forces such as magnetic fields (Amaral; Graham, D. L.; Ferreira, H. A.; Feliciano, N.; Freitas, P. P.; Clarke, L. A.; Amaral, M. D. Magnetic field-assisted DNA hybridization and simultaneous detection using micron-sized spin-valve sensors and magnetic nanoparticles. Sensors and Actuators, B: Chemical (2005), B107(2), 936-944) or hydrostatic pressure (Pressure Biosciences; Green D J, Litt G J, Laugharn J A Jr. Use of high pressure to accelerate antibody: antigen binding kinetics demonstrated in an HIV-1 p24: anti-HIV-1 p24 assay. Clin Chem. 1998 February; 44(2):341-2).

It is known that an electric field can be used to control DNA transport and hybridisation and therefore it has been used with microchip-based nucleic acid arrays (Nanogen; Edman C F, Raymond D E, Wu D J, Tu E, Sosnowski R G, Butler W F, Nerenberg M, Heller M J., Electric field directed nucleic acid hybridization on microchips. Nucleic Acids Res. 1997 Dec. 15; 25(24):4907-14 and Georgiadis; Heaton R J, Peterson A W, Georgiadis R M. Electrostatic surface plasmon resonance: direct electric field-induced hybridization and denaturation in monolayer nucleic acid films and label-free discrimination of base mismatches. Proc Natl Acad Sci USA. 2001 Mar. 27; 98(7):3701-4).

It is also known that an AC electric field can be used to manipulate DNA because DNA is highly polarisable and when exposed to an electric field, a dipole is induced along the backbone of the DNA (C Wälti et al AC electrokinetic manipulation of DNA, 2007 *J. Phys. D: Appl. Phys.* 40 114-118). It is also known that AC can be used in dielectrophoresis to collect DNA on microelectrodes depending upon the applied frequency (Bakewell D J, Morgan H. Dielectrophoresis of DNA: time- and frequency-dependent collections on microelectrodes. IEEE Trans Nanobioscience. 2006 March; 5(1):1-8).

However, there is still a need to provide improved method of heterogeneous capture probe based assays with reduced assay time and improved sensitivity.

Accordingly, the present invention provides a method for processing a sample, which method comprises:
a) contacting a binding phase, which binding phase is capable of binding an analyte, with the sample in the presence of a medium;
b) applying across the medium a first alternating field composed of a plurality of pulses and having a first frequency, a first pulse duration and a first pulse rise time;
c) optionally applying across the medium a second alternating field; and
d) thereby influencing the sample and/or the binding phase in the medium.

In an alternative embodiment, the present invention also provides a method for processing a sample, which method comprises:
a) contacting a binding phase, which binding phase is capable of binding an analyte, with the sample in the presence of a medium;
b) applying across the medium a first alternating field having a first frequency;
c) applying across the medium a second alternating field; and
d) thereby influencing the sample and/or the binding phase in the medium.

In this embodiment, the first alternating field is preferably composed of a plurality of pulses and has a first pulse duration and a first pulse rise time. It is further preferred that the second alternating field of this embodiment is composed of a plurality of pulses and has a first pulse duration and a first pulse rise time.

The present invention also provides a device for processing a sample optionally comprising an analyte, wherein the device comprises a medium, a binding phase capable of capturing the analyte, a plurality of electrodes and an electric field source for applying at least two alternating fields across the medium, wherein the device is capable of applying at least one alternating field is composed of a plurality of pulses. Preferably, each alternating field comprises a plurality of pulses and has a unique combination of parameters selected from frequency, pulse duration and pulse rise time.

The present invention will now be described in more detail.

The wording "alternating field" means that an electric field which has a non-constant value which may be created, for example, by applying alternating current (AC) or an alternating voltage to a pair of electrodes.

The wording "alternating field composed of a plurality of pulses" means more than one application of the alternating field, typically in immediate succession, for example by switching the applied field on and off, or by reducing and then increasing the field (or vice versa).

The wording "applying a second alternating field" and "applying one or more further alternating fields" may mean that a second or one or more further alternating fields are applied simultaneously with the first alternating field. For example, the two or more alternating fields may be a series superimposed fields, each having different frequencies and/or shapes, such as sinusoidal or square. For example, a high frequency sinusoidal alternating field and low frequency sinusoidal alternating field may be superimposed and applied simultaneously. Alternatively, the second or one or more further alternating fields may be applied sequentially after the first alternating field.

In step (d) of the method according to the present invention the sample and/or the binding phase is influenced by the application of the first alternating field and optionally also by the second optional alternating field. In one embodiment, the sample is influenced by movement of the analyte through the medium towards the binding phase. Alternatively or additionally, the sample and/or the binding phase is/are influenced to promote binding of the analyte to the binding phase. In this embodiment, the sample may be influenced to promote binding of the analyte to the binding phase by for example, being concentrated at the binding phase. The binding phase may be influenced, for example, by being orientated in a direction, which promotes binding of the analyte. In one embodiment wherein the binding phase comprises a capture probe, the position and/or orientation of capture probe may be influenced to promote binding of the analyte to the capture probe. In this embodiment, wherein the binding phase is a plurality of electrodes, the analyte and/or the capture may be influenced to bind to the electrodes and/or between the electrodes.

In a preferred embodiment, the first alternating field controls movement of the analyte through the medium towards the binding phase and the second alternating field promotes binding of the analyte to the binding phase.

The present method is preferably directed to analytes that are bio-molecules, although any charged or polarisable analytes may be assayed, if desired. In preferred embodiments, the analyte comprises one or more compounds selected from a cell, a protein, a polypeptide, a peptide, a peptide fragment, an amino acid, a carbohydrate, a lipid, a synthetic chemical or nucleic acid such as DNA or RNA.

The method according to the present invention is particularly advantageous for assaying analytes which have electrical properties which allow them to exhibit a strong dielectrophoretic activity in the presence of an alternating field. Accordingly, analytes which exhibit effective polarizability in an alternating field are particularly suited to the present method. In this regard, the assay method is particularly useful for detecting DNA or RNA which can be easily manipulated using alternating field.

The sample typically comprises a biological sample such as a cellular sample. The biological sample may or may not need to be pre-treated, depending on its structure.

The present inventors have surprisingly found that application of a first alternating field and a second alternating field to a medium comprising a sample reduces the time and increases the sensitivity of a method for processing the sample.

The present inventors have also surprisingly found that application of a first alternating field composed of a plurality of pulses and optionally a second alternating field to a medium comprising a sample reduces the time and increases the sensitivity of a method for processing the sample.

Preferably the second alternating field is composed of a plurality of pulses and has a second frequency, a second pulse duration and a second pulse rise time.

In a preferred embodiment, a first alternating field and second alternating field are applied to the medium and the first alternating field and second alternating field are different. In this embodiment, the first and second alternating field may differ by their frequency and/or pulse duration and/or pulse rise time and/or amplitude.

The inventors have unexpectedly found that more than one alternating field, which may be pulsed and are preferably different, can be used to manipulate an analyte and/or a binding phase and improve the speed and efficiency of a method of processing a sample. The alternating fields are able to control different events which occur during the method, including bulk events, such as movement of the analyte through the medium to the binding phase, and surface confined events, such as binding of the analyte to the binding phase. Accordingly, the first alternating field may be used to control movement of the analyte through the medium to the binding phase, for example movement of DNA through the medium to the binding phase. The first and/or the second alternating field may be used to control binding of the analyte to the binding phase, for example DNA hybridisation. In one embodiment, the first and/or second alternating field may be used to position and/or orientate the capture probes attached to the binding phase, for example by elongation, (as described by Waelti C. et al 2007), to enhance the hybridization efficiency. The first and/or second alternating field may also be applied after the analyte has bound to the binding phase to remove unspecifically bound analyte any adsorbed analyte and improve the washing efficiency. For example, an alternating field may be applied during washing with a buffer. If the buffer used for washing has a high ionic strength this induces negative dielectrophoresis and unspecific bound analytes, such as DNA, would be driven to the region of lower electric fields away from electrodes. This is particularly useful when electrodes act as the binding phase because it is easy to remove unspecific bound analytes away from the electrodes.

The present inventors have also found that if the alternating field applied comprises a plurality of pulses the manipulation of an analyte and/or a binding phase is improved and, therefore, the speed and efficiency of a method of processing a sample is improved.

The frequency and amplitude of the alternating fields is set at a suitable level which allows for optimal polarity of the analyte being processed thereby allowing selective manipulation and movement of the target analyte and/or the binding phase. The specific frequency and amplitude required for each alternating field will depend upon the type of sample being processed, the electrical properties, density, shape and size of the target analyte. The specific frequency and amplitude required for each alternating field will also depend on the medium used in the method. For example, if the analyte is DNA and electrodes act as the binding phase, binding of DNA to electrodes is strongly dependent on the ionic strength of the medium (polarizability of the medium). Accordingly, the conductivity of the medium will affect the frequency and amplitude of the alternating field required.

In the embodiment, wherein the alternating field comprises a plurality of pulses, the pulse rise time and frequency of the alternating field is set at a suitable level which allows for optimal acceleration of the analyte through the medium. The specific pulse rise time and frequency required for each alternating field composed of plurality of pulses will depend upon the type of sample being processed, the electrical properties, the density, shape and size of the target analyte and the medium used in the method. Without being bound by theory it may be that a large pulse rise time and low frequency may be required for larger analytes to allow sufficient force to be applied for sufficient time to cause them to move.

In the embodiment, wherein the alternating field comprises a plurality of pulses, the pulse duration of the alternating field is set at a suitable level which allows for optimal speed of movement and distance of movement of the analyte through the medium. The specific pulse duration required for each alternating field composed of a plurality of pulses will depend upon the type of sample to be processed, the electrical properties, the density, shape and size of the target analyte and the medium used in the method. Without being bound by theory it may be that a large pulse duration may be required for larger analytes to provide sufficient force to move them or for analytes to be moved over longer distances.

The first and second alternating fields may be applied either simultaneously or sequentially depending upon the type of events to be controlled in the assay device. In one embodiment both the first and second alternating fields are composed of a plurality of pulses. In the embodiment wherein the first and second alternating fields are applied sequentially the voltage, and/or frequency and/or pulse duration and/or pulse rise time of the first alternating field may be changed in order to produce the second pulsed alternating field. Preferably, the first and second alternating field are applied simultaneously.

The first and second alternating fields may differ by their frequency and/or amplitude and/or pulse duration and/or pulse rise time.

In the embodiment, wherein the alternating field(s) is/are composed of a plurality of pulses, the number of pulses applied is not particularly limited and may be in the range 1 to the total number of cycles possible in the time period of the alternating field application.

Each alternating field is preferably applied for a period of time of 1 to 20 minutes, preferably 5 to 20 minutes, more preferably from 10 to 20 minutes.

In a preferred embodiment, wherein the first alternating field is used to control movement of the analyte through the medium to the binding phase, the first alternating field preferably has a frequency of 1 to $10^9$ Hz more preferably $10^4$ to $10^7$ Hz. This range of frequency may improve analyte movement by inducing dipolar charge on the analyte throughout the medium, particularly for DNA. There may be a decreasing effect on analyte movement when higher frequencies than $10^7$ Hz are used, as there is progressively less time for induced dipoles to form and for transport to occur.

The first alternating field, which may be pulsed, preferably has field strength of 10 kV/m to 1000 MV/m.

The first alternating field, which may be pulsed, preferably has a frequency of 30 Hz and a voltage of 350 mV.

The second alternating field, which may be pulsed, preferably has a frequency of $10^2$ to $10^9$ Hz.

The second alternating field, which may be pulsed, preferably has a voltage of 10 mV to 5 V.

In a preferred embodiment, wherein the second alternating field is composed of a plurality of pulses and is used to promote binding of the analyte to the binding phase, the second pulsed alternating field preferably has a pulse duration of $10^{-2}$ s to $10^{-8}$ s. Preferably the second pulsed alternating field also has a pulse rise time of $10^{-8}$ s to $10^{-10}$ s. This pulse duration and pulse rise time may improve surface confined events, particularly for DNA hybridisation.

The first alternating field and second alternating field preferably have waveforms independently selected from sinusoidal, square, sawtooth and triangular.

The assay method according to the present invention may further comprise one or more steps of applying one or more further alternating fields. The further alternating fields may be used to control different assay events from the first and second alternating fields including the elongation of capture probes to aid hybridisation of the analytes to the capture probes and the removal of unspecific bound analytes, as discussed above. In this embodiment each of the further alternating fields preferably has a frequency that is unique in relation to the frequency of all other alternating fields. In the embodiment wherein each further alternating field is composed of a plurality of pulses each further alternating field preferably has a combination of frequency, pulse duration and pulse rise time that is unique in relation to that combination for all other alternating fields. Accordingly the $1^{st}$ alternating field, $2^{nd}$ alternating field and each further alternating field applied each have a unique combination of these parameters.

Further alternating fields preferably have a frequency of $10^2$ to $10^9$ Hz. Further alternating fields preferably have a voltage range of 10 mV to 5 V. Further alternating fields preferably have a pulse duration of $10^{-2}$ s to $10^{-8}$ s. Further alternating fields preferably have a pulse rise time of $10^{-8}$ s to $10^{-10}$ s.

The first and optional second and further alternating fields are preferably applied to the medium using plurality of electrodes. The plurality of electrodes are preferably in the form of an interdigitated electrode structure. An example of an interdigitated electrode structure is shown in FIG. 1. FIG. 1 shows a complete mask layout of the gold interdigitated microelectrode structures, including four device chips, alignment marks and dummy metal lines to speed lift-off processing. The number of digits (N) on each electrode is preferably from 5 to 10. The length of each digit (L) is preferably from 75 to 150 µm. The width of each digit (W) and the width of the gap between each digit (G) is each preferably from 1.5 to 10 µm and W and G are preferably the same.

Examples of electrode structures which may be used in the present invention are also shown in FIGS. 2, 3 and 4.

Figure 14:
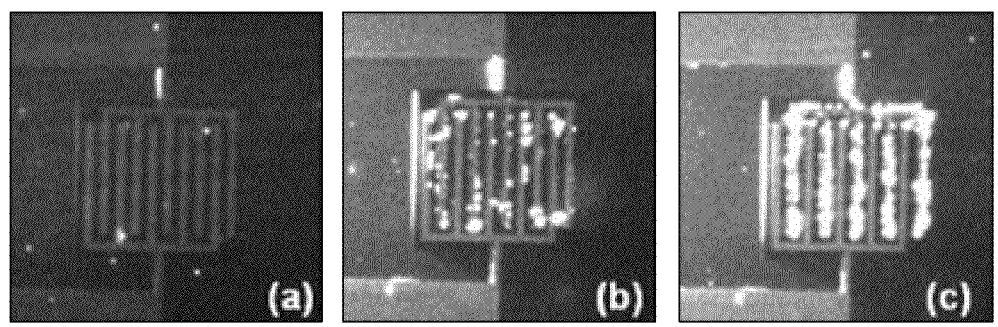

FIG. 14 shows a gold IDE electrode immobilised with complementary probe, in a solution 1 nM Qdots in 3 mM HEPES buffer, pH 6.9. (a) Field off, (b) The IDE was connected to an AC field of 2 V at 100 kHz for 6 min, (c) The IDE was connected to an AC field of 2.5 V at 100 kHz for an extra 6 min.

Figure 15:
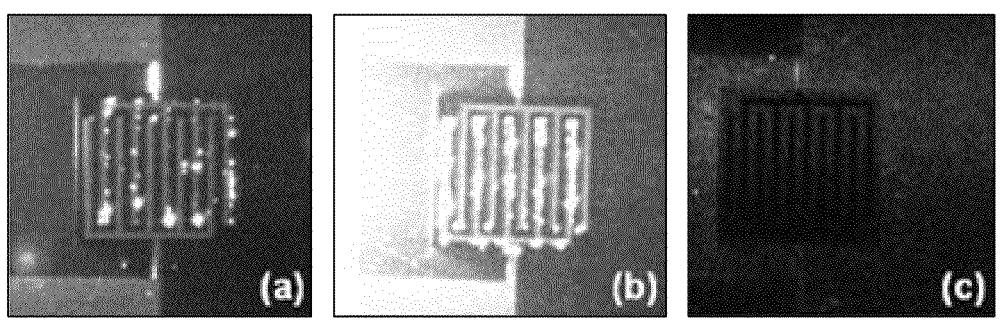

FIG. 15 shows two Gold IDE electrodes immobilised with complementary probe connected to an AC field of 2.5 V at 100 kHz for 10 min. The electrodes were immersed in 3 mM HEPES buffer solution containing (a) 1 nM Qdots and 1 nM target, (b) 1 nM Qdots and 10 nM target (c) Shows (b) after washing in SSC+SDS solution.

The method according to the present invention may be used to purify the analyte, isolating the analyte or sort the analyte. The method according to the present invention is preferably an assay method for detecting the presence or absence of the analyte in the sample. In this embodiment, the assay method may also comprise quantifying the sample.

In one embodiment, the method according to the present invention further comprises one or more steps of washing after the analyte is bound to the binding phase. In this embodiment, an alternating field may be applied in order to remove unbound and/or unspecific bound analyte, as discussed above.

Techniques to purify, isolate, sort and quantify analyte in a sample are well known by the person skilled in the art and accordingly the method according to the present invention can be easily adapted for carrying out the specific processing of the analyte required.

In one embodiment, wherein a plurality of electrodes used to apply the alternating field is the binding phase, the bound analyte, such as DNA, may be detected at the electrode either optically or electrochemically (e.g. by electrochemical impedance spectroscopy EIS).

If the method according to the present invention is used to isolate the analyte, the method may further comprise a step of separating the binding phase with the analyte bound thereto from the medium. Any conventional separation step known to the person skilled in the art for separating the binding phase from the medium is applicable. The present method may also further comprise a step of eluting the analyte from the binding phase.

The method according to the present invention may be used in a macro-scale environment or a micro-scale environment. If the method is used in a macro-scale environment, the analyte may be detected when bound to the binding phase after a step of washing. If the method is used in a micro-scale environment, the analyte may need to be separated from the binding phase and the medium for further downstream processing and analysis. Typically the present method may be employed in a fluidic device, such as a microfluidic or nanofluidic device.

The method according to the present invention may further comprise a lysis step comprising subjecting the sample to electrochemical or chemical conditions to lyse the sample. The method according to the present invention may also include a step of transfection when the sample comprises cells, for example, a technique called electroporation may be used in the method.

The binding phase must be capable of binding the analyte but is not limited to any specific material. The skilled person would easily be able to select a suitable binding phase for use in the present method depending upon the analyte to be detected. Various materials are known to bind analytes, such as nucleic acid binding solid phases including silica-based materials, polymeric materials and other materials such as glasses. The form of the solid phase includes sheets, filter paper, sieves, sinters, webs and fibres. Particles or beads, including magnetic particles or beads, are particularly useful as these may be packed in a column or used in suspension and have high binding capacity.

The analyte may bind directly to the binding phase or the solid phase may comprise a capture probe which is specific for the analyte to be detected and capable of reacting with the analyte to capture it on the solid phase. For example, a DNA probe may be used to capture a specific DNA target sequence by hybridisation. The skilled person would easily be able to use suitable capture probes depending upon the analyte to be detected.

In one embodiment, the binding phase is one or more electrodes which apply the alternating fields. This embodiment is particularly suitable when the analyte is DNA wherein the DNA is collected at the region of high electric fields at the electrodes.

In this embodiment, the analyte may bind directly to the electrodes or capture probes specific for the analyte, and capable of reacting with the analyte, may be immobilized on the electrodes to capture the analyte.

The medium used in the method of the present invention is any suitable medium, including liquids and gels and buffered solutions, which allows the analyte to move through it and bind to the binding phase. The medium may also comprise an electrolyte facilitating the alternating fields to flow through and preferably, in order to obtain a positive dielectrophoresis, the polarizability of the medium is lower than that of the analyte.

The skilled person may select suitable media depending upon the type of analyte to be detected.

The assay device according to the present invention is suitable for carrying out the method of the present invention as described above. The medium and binding phase are as described above in respect of the method of the present invention.

The electric field source is preferably capable of applying two simultaneous or sequential alternating fields, each having a unique combination of parameters including frequencies and/or pulse durations and/or pulse rise times. At least one of the alternating fields is composed of a plurality of pulses. In one embodiment, each alternating field is composed of a plurality of pulses. The alternating fields may be applied either simultaneously or sequentially. In one embodiment, the electric field source is also capable of applying one or more further alternating fields, preferably each composed of a plurality of pulses, and having a unique combination of parameters including frequencies and/or pulse durations and/or pulse rise times.

The electric field source in the assay device preferably comprises a plurality of electrodes. In this embodiment, the plurality of electrodes may be in the form of an interdigitated electrode structure, as shown in FIGS. 1 to 4 and discussed above with respect to the method of the present invention.

In one embodiment, the device according to the present invention may be in the form of a microchip comprising a microarray of microspots forming the binding phase, preferably comprising probe molecules such as immobilized oligonucleotides, and a micro-electrode arrangement. Microchips and microarrays are well known to the person skilled in the art.

Typically the present device may be a fluidic device, such as a microfluidic or nanofluidic device.

The present invention also provides the use of two or more alternating fields to influence a sample and/or a binding phase capable of binding an analyte. Preferably each alternating field is composed of a plurality of pulses. In a preferred embodiment each alternating field has a combination of frequency, pulse duration and pulse rise time that is unique in relation to that combination for all other alternating fields. Preferably the sample and/or binding phase is/are influenced to control movement of an analyte towards a binding phase and/or binding of the analyte to the binding phase.

The present invention also provides the use of one or more alternating fields, wherein each alternating field is composed of a plurality of pulses, to influence a sample and/or a binding phase capable of binding an analyte.

As mentioned above, the present invention is made on the basis that the application of two alternating fields or the application of one or more pulsed alternating fields may be used to control specific events when processing a sample including transport of the target analyte from the bulk solution to the detector binding phase and binding of the analyte to the binding phase. Accordingly, the processing method is quicker and more sensitive. The present invention is particularly useful for nucleic acid (e.g. DNA) assays because DNA is polarisable and, therefore, moves in an alternating field. However, the present invention may be employed for many different types of assays for different analytes well known to the person skilled in the art.

EXAMPLES

In the following Examples, the effect on hybridization efficiency of applying the AC fields used in the invention was investigated by electrochemical impedance spectroscopy (EIS) and fluorescence detection.
Protocols Two samples were investigated: Fluorescently labelled 1 µm polystyrene beads and Qdot 605-streptavidin-conjugates. The 1 µm diameter polystyrene beads were obtained from Invitrogen. 100 µL of the 2% bead solution was diluted with 4.9 ml of distilled water. A 1 nM solution of Qdot was also prepared in distilled water.

Figure 1:
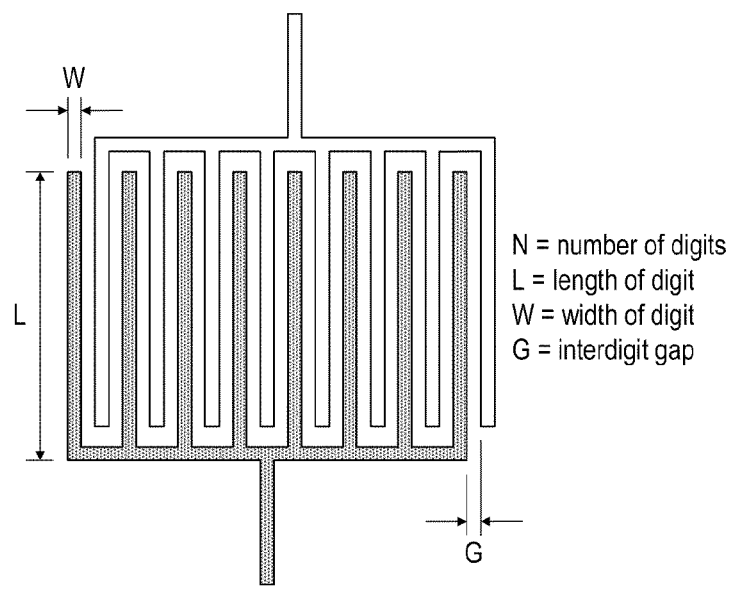
Figure 2:
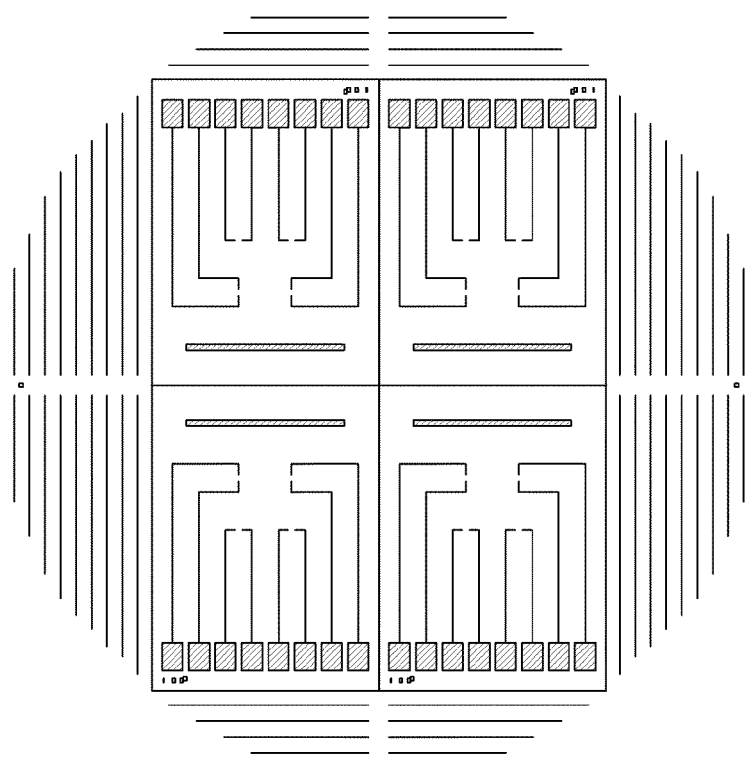
FIG. 2 shows a complete mask layout of the gold interdigitated microelectrode structures including four device chips, alignment marks and dummy metal lines to speed lift-off processing.
Figure 3:
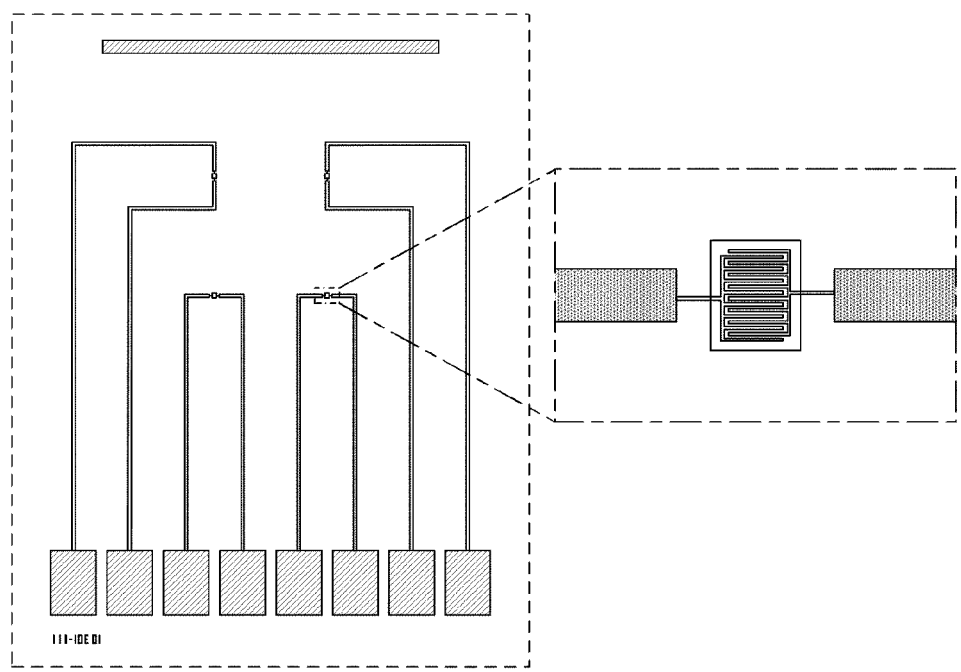
FIG. 3 shows an individual layout of a chip, with four identical 10 µm interdigitated electrode pairs device structures, interconnect, bond pads and a frame alignment marker. Each electrode has five digits with digit width and interdigit spacing of 10 µm, and a digit length of 150 µm.
Figure 4:
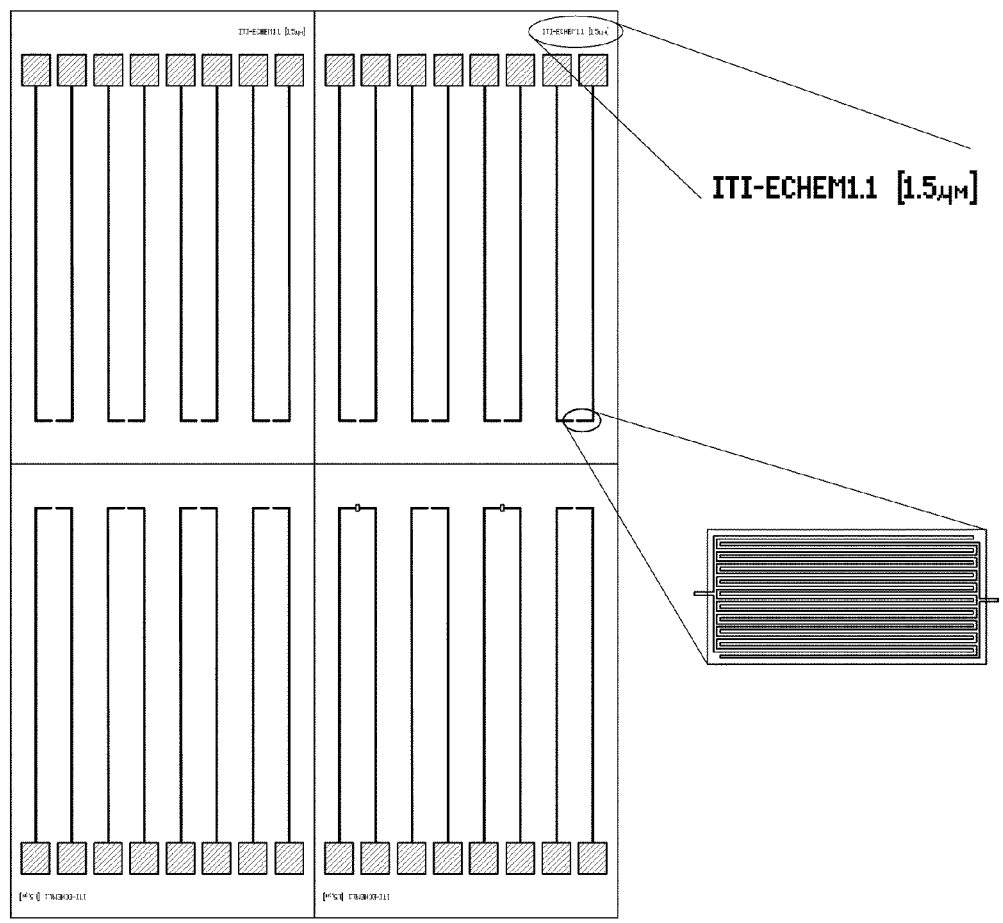
FIG. 4 shows a Mask design, showing blow-ups of the chip labelling and of a 1.5 µm interdigitated structure.
Figure 5:
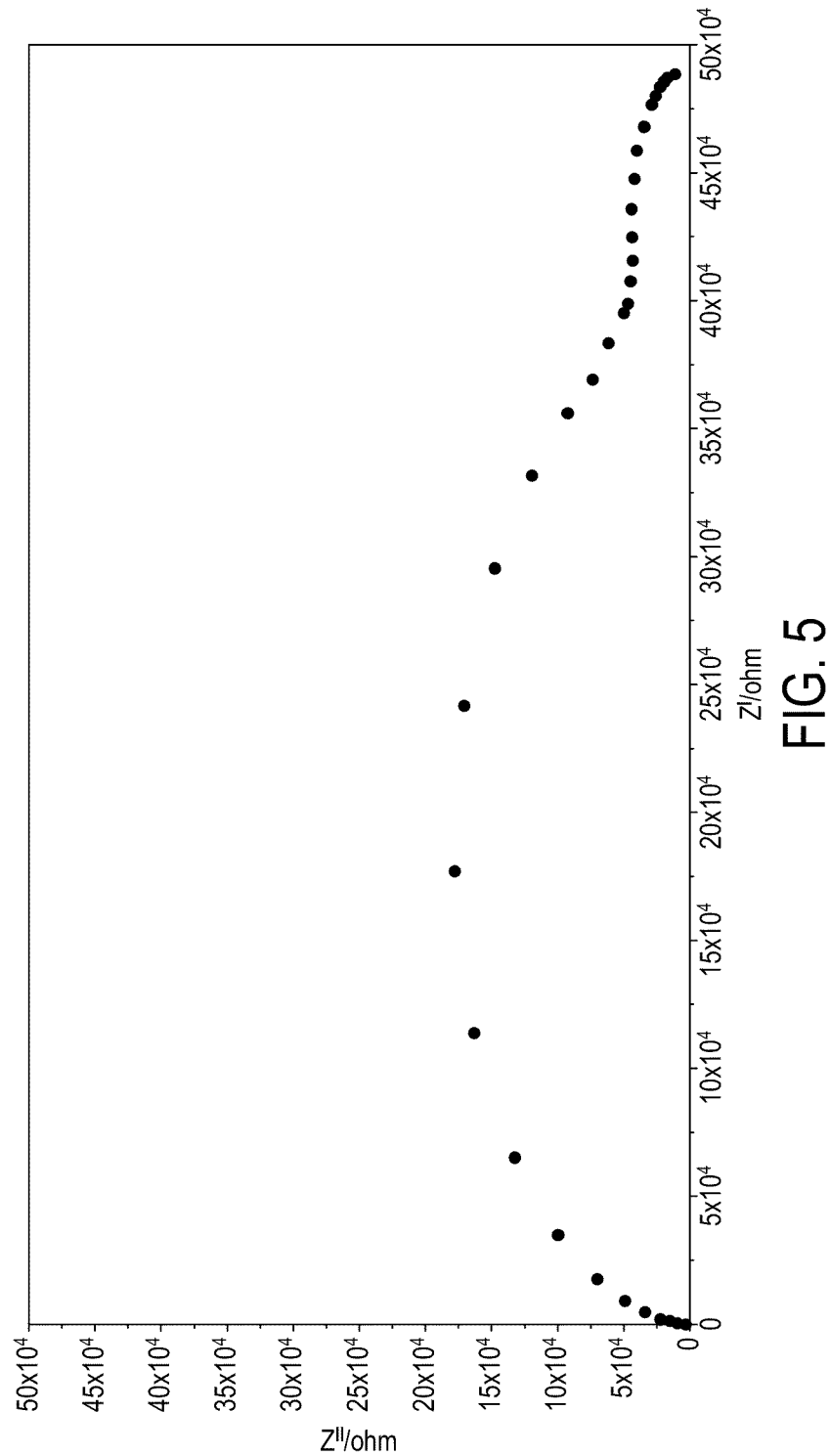
FIG. 5 shows Nyquist plots of a gold interdigitated electrode used for dielectrophoresis (DEP) measurements.

Prior to the experiment, an electrode control was performed by measuring the impedance of the interdigitated electrodes (IDE). This was done in a solution of 10 mM [Fe(CN)6]3-/4- by applying a 10 mV rms amplitude voltage at frequencies between 1 MHz and 0.1 Hz to the electrode with a potentiostat. The characteristic semi-circle observed (FIG. 5) confirmed that both IDE electrodes and connections were properly working.

After emptying the flow cell and thoroughly cleaning the electrodes with distilled water, the solution of polystyrene beads was injected into the flow cell and the potentiostat replaced by a 50 MHz Pulse Generator (HP 8112A). The sample was excited with a 470 nm pulsed laser diode and the fluorescence collected through a 10× objective and sent onto a cooled EMCCD camera (−70° C.) via a 535 nm 40 nm bandpass filter.
Dielectrophoresis (DEP) of Microspheres The effect of the magnitude of applied AC voltage (and hence field) and frequency applied to the IDEs was studied experimentally on observed DEP over a frequency range spanning from 50 MHz to 20 kHz and an applied peak voltage up to 8 V.

Figure 6:
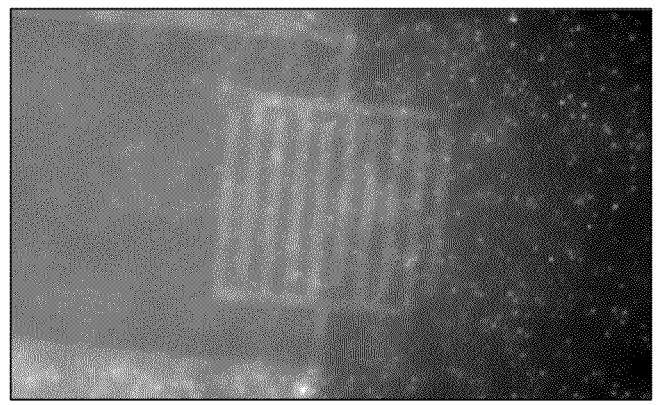
FIG. 6 shows a gold electrode (IDE) in a solution of polystyrene beads. The IDE was connected to an AC field of 7 V at 50 MHz.

At the highest frequencies, it was observed that the beads were homogeneously distributed within the field of view, even when a relatively high voltage was applied. This is clearly observed (FIG. 6) for 7 V at 50 MHz.

Figure 7:
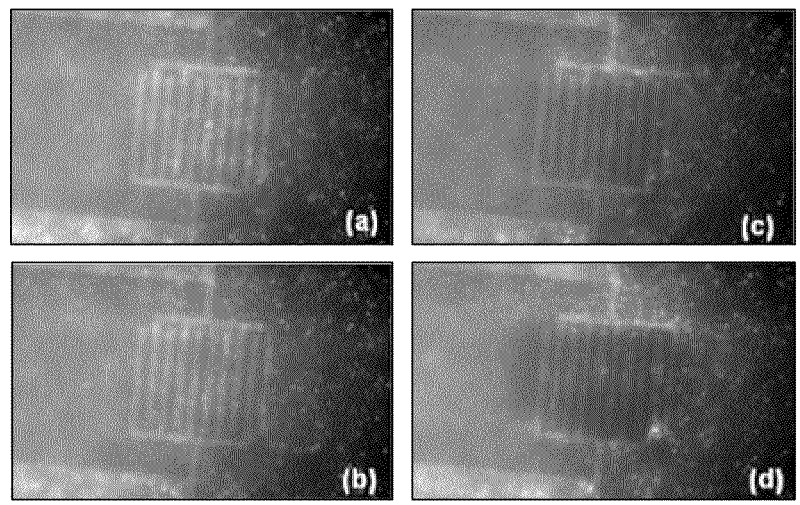
FIG. 7 shows a gold IDE electrode in a solution of polystyrene beads. Images were recorded with different applied voltages at a frequency of 100 kHz. (a) 2V, (b) 4V, (c) 6V & (d) 8V.
Figure 8:
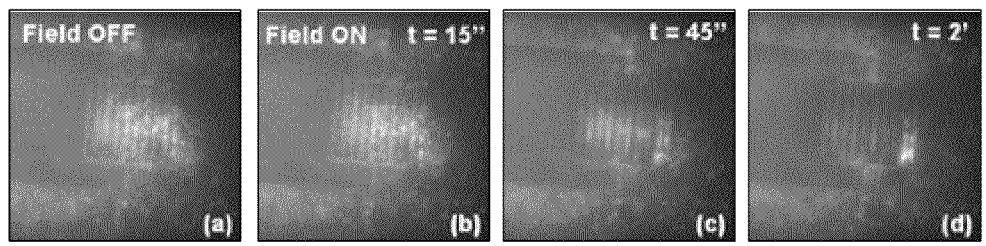
FIG. 8 shows a gold IDE electrode in a solution of polystyrene beads. Images were recorded with an applied voltage of 8 V at a frequency of 100 kV at different time interval. (a) Field OFF reference time, (b) Field ON (15"), (c) Field ON (45") & (d) Field ON (2').

On lowering the frequency to 100 kHz, it became possible to observe a reorganisation of the beads. FIG. 7 shows a series of images corresponding to different applied voltages. At 6 V (figure (c)) one can observe that the vertical part of the top electrode becomes brighter. At 8 V a dark area starts to appear showing the field geometry across the IDE. The concentration of beads at the IDE becomes apparent within the first minute as shown (FIG. 8) although the response is still relatively weak at this frequency.

Figure 9:
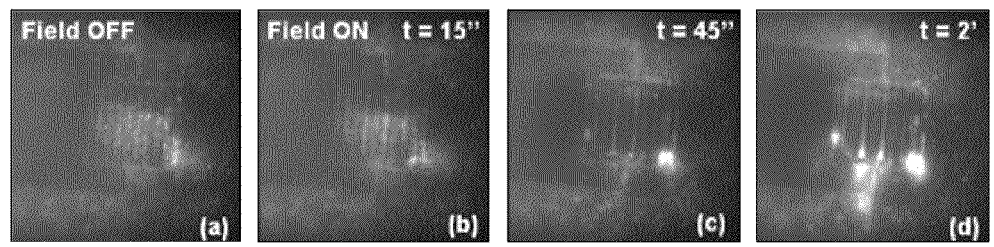
FIG. 9 shows a gold IDE electrode in a solution of polystyrene beads. Images were recorded with an applied voltage of 5 V at a frequency of 20 kV at different time interval. (a) Field OFF reference time, (b) Field ON (15"), (c) Field ON (45") & (d) Field ON (2').
Figure 10:
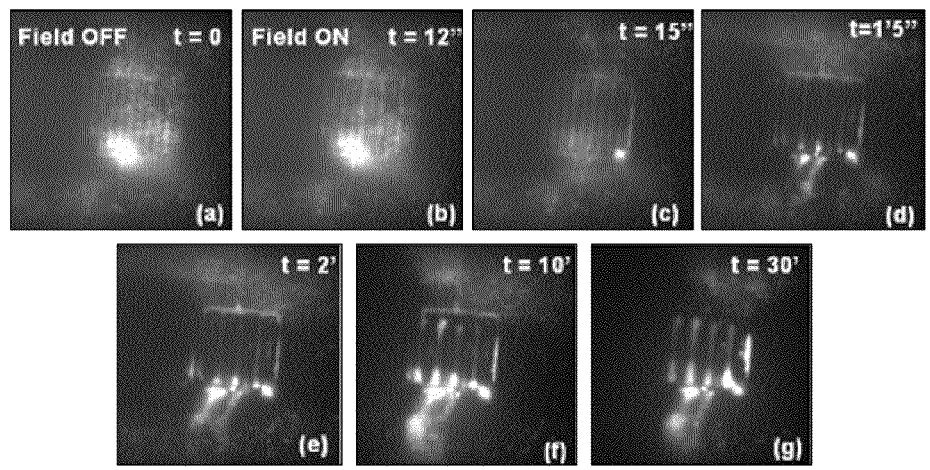
FIG. 10 shows a gold IDE electrode in a solution of polystyrene beads. Images were recorded with an applied voltage of 8V at a frequency of 20 kV at different time interval. (a) Field OFF reference time, (b) Field ON (12"), (c) Field ON (15"), (d) Field ON (1'5"), (e) Field ON (2'), (f) Field ON (10') & (g) Field ON (30').

When lowering the frequency down to 20 kHz at an applied peak voltage of 5 V, the signal becomes significantly brighter as shown (FIG. 9). FIG. 10 shows a series of images recorded with an applied voltage of 8 V. As the spacing between electrodes is 10 µm, the root mean squared (rms) field across the electrode is approximately $5.7 \times 10^5$ V m$^{-1}$ and even higher at the tip of the electrode due to local enhancement. The time series presented FIG. 10 shows clearly that the beads start first to condensate on the tip fingers (top electrode) and gradually cover the length of the electrode fingers.
DEP of Quantum Dots and Quantum Dots with Bound Target DNA A series of experiments was carried out to investigate the trapping of Qdots on gold IDEs. The trapping of relatively small DNA fragments (less than 10 kbp) requires extremely high field strengths, of the order of $10^7$ V rms m$^{-1}$. However the response of the relatively large Qdots should be much greater. Here the approach was to use Qdot labels as a DEP vector to trap target DNA bound to Qdots via streptavidin-biotin interaction at the electrode, therefore achieving localised DNA concentration using lower field strengths. Three DEP experiments were conducted using the following solutions: Qdot in distilled water, Qdot in HEPES buffer (required for hybridization), and finally Qdot labelled target in HEPES buffer.

Figure 11:
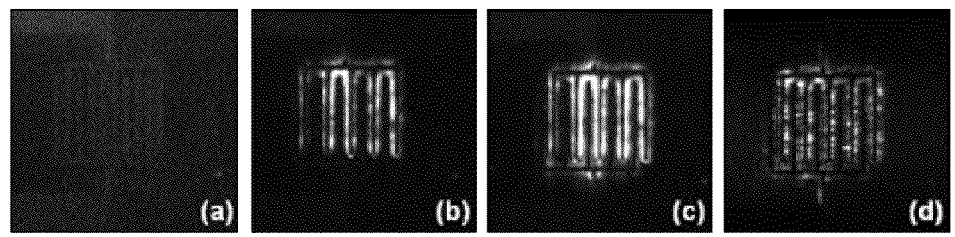
FIG. 11 shows a gold IDE electrode in a solution of 1 nM Qdots in distilled water. (a) Field off, (b) The IDE was connected to an AC field of 2V at 1 MHz for 6 min, (c) same as (b) with reverse polarisation (d) the electrode was measured after being left 12 hours in distilled water without field.

FIG. 11 shows an electrode immersed in 1 nM of Qdots dissolved in distilled water. When an AC field is applied (here 1 MHz, 2 V peak voltage) for several minutes, the Qdot can be seen to concentrate at the periphery of the electrode fingers, clearly revealing the shape of the attractive electrode (b) in the IDE pair. When the polarity was reversed, the opposite electrode become attractive as expected and as shown in FIG. 11(c). It was also observed that once the Qdots have been concentrated at the electrode, the latter tend to stay there as shown in FIG. 11(d), where the electrode is displaying a strong signal even after 12 h in distilled water. This is consistent with high concentration Qdot coagulation and electrode adsorption.

Figure 12:
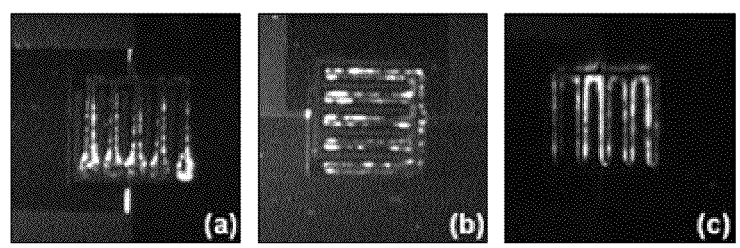
FIG. 12 shows three Gold IDE electrodes in a solution 1 nM Qdots in distilled water. Each electrode was connected for a duration of 6 min to an AC field of 2V at 20 KHz (a), 100 kHz (b) and 1 MHz (c).
Figure 13:
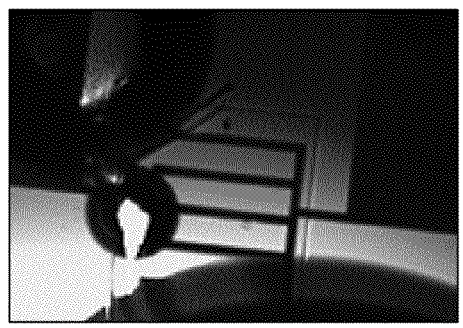
FIG. 13 shows Transmission image of a damaged IDE. The image was recorded after applying an AC field of 5 V at 20 kHz.

This experiment was then repeated over a range of frequencies. FIG. 12 shows the result obtained with an applied AC field of 2 V at 20 kHz, 100 kHz and 1 MHz. At the lowest frequency (a) the Qdots are mostly attracted to the tip of the electrode fingers where the field strength is the highest. At higher frequencies ((b) & (c)), the attraction of the nanoparticles was observed to be more homogeneous. Typically, best results were obtained at 100 kHz with an applied peak voltage between 2 and 3 volts (of the order of $2 \times 10^5$ V rms m$^{-1}$). At higher voltages, the formation of bubbles and ultimately damage to the electrode was observed, as shown in FIG. 13. (The picture shows that only one electrode is present, the other one has completely detached.)

Hybridization is usually conducted in a buffer solution such as SSC. However, such a solution has been shown to lead to less favourable results than when used in combination with these DEP experiments. To circumvent this effect the DEP of Qdots was investigated in an alternative hybridization buffer, HEPES (3 mM, with 1 mM NaOH, pH 6.9), which has a conductivity of approximately 20 $\mu$S cm$^{-1}$. The results presented (FIG. 14) show the successful build up of Qdots at the attractive electrode through DEP after 6 and 12 mins.

Finally, the DEP of Qdot-labelled target DNA is shown (FIG. 15) for 1 nM and 10 nM target concentration. Figs. ($a$) and ($b$) demonstrate that this labelled DNA can be efficiently concentrated at the electrodes via DEP of the Qdot label. It is interesting that, unlike Qdots, the Qdot labelled DNA does not appear to be irreversibly adsorbed at the electrode surface (FIG. 15($c$)).

CONCLUSION

The results presented above show that positive DEP can be used to attract and concentrate both polystyrene beads and nanocrystal Qdots at the electrode surface. As beads and Qdots can be functionalised to bind to DNA as labels, DEP of these species can be used to concentrate a specific labelled target at the electrode on the timescale required for near patient environment detection in hybridisation compatible solutions. This opens up the possibility of using Qdot labelling of DNA for fluorescence detection and DEP transport, with its potential to speed up hybridization process.

In more detail, application of an AC field during hybridization of target DNA on probe-modified, interdigitated gold microelectrodes yielded a substantially enhanced hybridization efficiency, which could be clearly discriminated from unspecific binding of non-complementary DNA.

The response after AC field application was one order of magnitude higher, as compared with hybridization without the AC field. An increase in the electron transfer resistance up to 5 min AC field application in the absence of target DNA was also observed. This might be explained with a re-orientation of the surface bound probe layer making it more accessible to the target molecules.

In summary, and without being bound by theory, the enhanced hybridization efficiency during AC field application might be caused by the re-orientation of the probe layer or the increase of the local target concentration by AC field-induced dielectrophoretic trapping of target oligonucleotides or by a combination of both of these phenomena.

In order to further investigate possibilities to concentrate analytes on the site of interdigitated electrodes, the effect of a wide range of frequencies and voltage amplitudes on the dielectrophoretic trapping of 1 $\mu$m size fluorescent microspheres and on streptavidin/quantum dot-conjugates in the set-up for combined detection was tested, and analysed it by TIRF. These experiments demonstrated the concentration of beads and Qdots on the surface of interdigitated electrodes applying AC fields of 20 kHz with an amplitude of 5 to 8 V. The possibility to concentrate Qdot-streptavidin-conjugates on the site of surface immobilized probes implicates the possibility to concentrate any kind of target via biotinylated detection probes or biotinylated secondary antibody.

The invention claimed is:

1. A method for processing a sample, which method comprises:
   a) contacting a binding phase, which binding phase is capable of binding an analyte, with the sample in the presence of a medium;
   b) applying across the medium a first alternating field composed of a plurality of pulses and having a first frequency, a first pulse duration and a first pulse rise time;
   c) applying across the medium a second alternating field wherein the second alternating field is composed of a plurality of pulses and has a second frequency, a second pulse duration and a second pulse rise time; and
   d) thereby influencing the sample and/or the binding phase in the medium, wherein the method further comprises setting the pulse rise time, the frequency, and the pulse duration of the alternating fields for optimal acceleration and speed of movement of the analyte through the medium, to promote binding of the analyte to the binding phase,
   and wherein the first alternating field and the second alternating field have a different frequency, pulse duration and/or pulse rise time.

2. A method according to claim 1, wherein influencing the sample comprises moving the analyte through the medium towards the binding phase.

3. A method according to claim 1, wherein the first alternating field is capable of moving the analyte though the medium towards the binding phase.

4. A method according to claim 1, wherein the first and/or second alternating field has a frequency of 0.1 to $10^{10}$ Hz, preferably 30 to $10^9$ Hz.

5. A method according to claim 1, wherein the first and/or second alternating field has a field strength of 10 kV/m to 100 MV/m.

6. A method according to claim 1, wherein the second alternating field is capable of promoting binding of the analyte to the binding phase.

7. A method according to claim 1, wherein the first and/or the second alternating field has a pulse duration of $10^{-2}$ s to $10^{-8}$ s.

8. A method according to claim 1, wherein the first and/or the second alternating field has a pulse rise time of $10^{-8}$ s to $10^{-10}$ s.

9. A method according to claim 1, wherein the first and/or second alternating field has a frequency of $10^2$ to $10^9$ Hz.

10. A method according to claim 1, wherein the first and/or second alternating field has a voltage of 1 mV to 10V, preferably 10 mV to 5 V.

11. A method according to claim 1, wherein the first alternating field and second alternating field have waveforms independently selected from sinusoidal, square, sawtooth and triangular.

12. A method according to claim 1, wherein the first and second alternating fields are applied simultaneously or sequentially.

13. A method according to claim 1, which further comprises one or more steps of applying further alternating fields.

14. A method according to claim 13, wherein each further alternating field has a frequency that is unique to that of all other alternating fields.

15. A method according to claim 13, wherein each further alternating field is composed of a plurality of pulses.

16. A method according to claim 15, wherein each further alternating field has a combination of frequency, pulse duration and pulse rise time that is unique in relation to that combination for all other alternating fields.

17. A method according to claim 1, wherein the method is an assay method for detecting the presence or absence of the analyte in the sample, purifying the analyte in the sample, isolating the analyte in the sample or sorting the analyte in the sample.

18. A method according to claim 17, wherein the method is for detecting the presence of the analyte in the sample, wherein the method comprises quantifying the analyte.

19. A method according to claim 1, which further comprises a lysis step comprising subjecting the sample to conditions to lyse the sample.

20. A method according to claim 1, wherein the analyte comprises one or more compounds selected from a cell, a protein, a polypeptide, a peptide, a peptide fragment, an amino acid or a nucleic acid, such as DNA or RNA.

21. A method according to claim 1, wherein the binding phase comprises a capture probe, which capture probe is capable of reacting with the analyte to capture the analyte on the binding phase.

22. A method according to claim 21, wherein the position and/or orientation of capture probe is influenced to promote binding of the analyte to the capture probe.

23. A method according to claim 1, wherein the binding phase comprises a plurality of electrodes.

* * * * *